April 14, 1964 O. O. DUNHAM Plant Pat. 2,390
CHRYSANTHEMUM PLANT
Filed Sept. 7, 1962
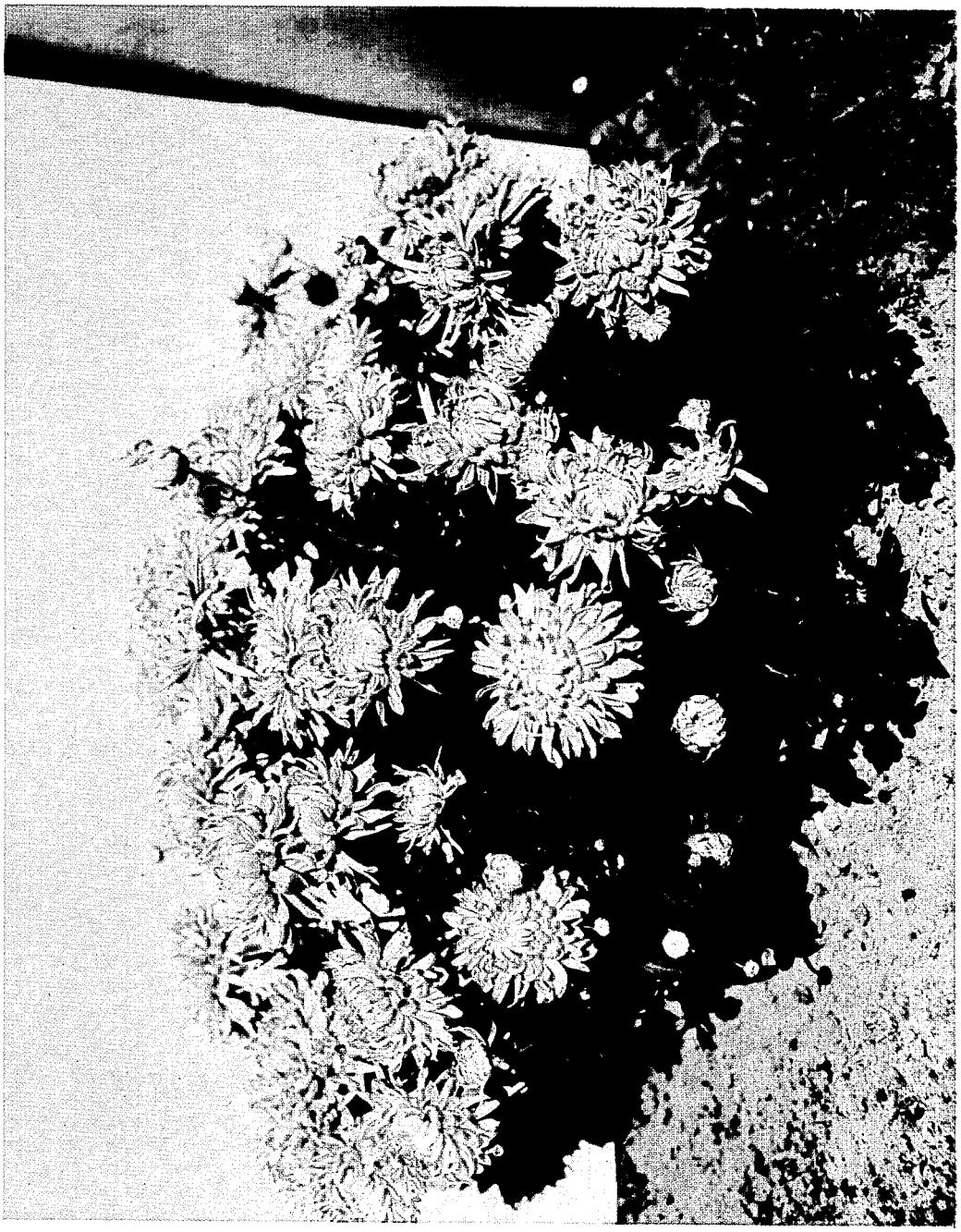
Inventor
O. O. Dunham
by Robb & Robb
attorneys United States Patent Office Plant Pat. 2,390
Patented Apr. 14, 1964

2,390
CHRYSANTHEMUM PLANT

Orville O. Dunham, Niles, Mich., assignor to George J. Ball, Inc., Chicago, Ill., a corporation of Illinois Filed Sept. 7, 1962, Ser. No. 222,252
1 Claim. (Cl. Plt.—79)

My present invention comprises a new and distinct variety of chrysanthemum plant which is the result of crossing the variety "Unity" an unpatented variety of my own introduction, with another variety of my own introduction, likewise unpatented and which I designate as seedling #5350.

The object of this invention has been to produce a new variety of chrysanthemum of the *indicum* type which retains the color of the pollen parent "Unity," which is a loosely incurving type, which will have a better flower formation than either parent, and retains the earliness to flower characteristic of the seedling #5350, and which will constitute an improvement over either of the parents with a more tightly incurving type of bloom and provide the desirable continuous blooming habit heretofore found to be a requisite of chrysanthemums.

This present new variety is the result of an intensive program of development which I have carried on for many years in the growth, cross breeding, selection and study of chrysanthemums of various types whether they be of the American Garden or other type. In conducting this program I have endeavored to take advantage of the best characteristics of each of the parents where possible and particularly of course the colors where found attractive with the earliness to bloom as well as compact upright growth with bushy plant habit primarily in the instant variety under consideration.

The result of the specific hybridization previously referred to has been to produce my present new and distinct variety of chrysanthemum characterized by its more tightly incurving blooms, the strong orange shading into moderate orange yellow color of the blooms, its compact, upright growth, bushy plant habit and early profuse and continuous blooming habit.

More specifically the blooms of my new variety are of the strong orange shading into moderate orange yellow color (Nickerson Color Fan published by the Munsell Color Company), the lighter color appearing toward the center of the flower with the darker colors shading the petals and providing thereby a mixed color in appearance. As grown in the vicinity of Niles, Michigan, in uniform culture, plants of my new variety have grown to an average height of approximately 24 inches with a spread of approximately 30 inches.

My new variety derives a number of characteristics from both parents, as has been previously stated but better characteristics than either separately and my new variety differs from both the parents and from other known varieties in many respects. As an example of comparison of my new variety with a previously known variety, which I have identified as "Bronze Giant," a variety of my own introduction and unpatented, I note that the color of the latter has been transmitted to the seedling hereof so as to produce the general bronze tone suggested by the name of one of the variety. The instant variety produces larger flowers than the variety "Bronze Giant," such flowers approximating 5½ inches in diameter.

Another feature transmitted from the parent is the earliness to flower which is by mid-September, with the instant variety producing flowers on shorter, bushier plants than the "Bronze Giant" with which is is compared.

Under the conditions of culture previously mentioned, which have been undertaken in the region of Niles, Michigan, plants of my new variety have grown very vigorously from early in the season, that is about mid-September, profusely and continuously until a killing frost. The plant itself is in the bush form with medium growth and branching in general form.

My new variety has been asexually reproduced by cuttings in the vicinity of Niles, Michigan.

My new variety has been found to retain its distincitive characteristics through successive asexual reproduction.

The accompanying drawing forming a part hereof shows a typical plant of my new variety of chrysanthemum in colors as nearly representative of the actual colors as is possible to obtain in photographic processes.

The following is a detailed description of my new variety of chrysanthemum plant, the color references being to the Nickerson Color Fan published by the Munsell Color Company:

*Description*

Parentage: Seedling.

*Seed parent.*—#5350 (unpatented variety of my own introduction).

*Pollen parent.*—"Unity" (unpatented variety of my own introduction).

Classification: *Chrysanthemum indicum.*

*Flower*

Blooming habit: Blooms profusely and continuously from mid-Septmber until a killing frost.

Observations were made in the vicinity of Niles, Michigan, during October.

Bud:

*Size:* Small

*Form:* Short with flat top

Somewhat affected by wet weather in that the petals burn and in hot weather the flower tends to fade more than otherwise.

Color:

*When sepals first divide.*—5YR 8/7.

*When petals begin to unfurl.*—7.5YR 7/11.

*When half blown.*—Inside of petals—7.5YR 8/8. Reverse of petals—10YR 8/10.

*Sepals.*—Smooth edge.

*Caly.*—Shape — funnel. Size — large and broad. Aspect—smooth.

No odor when rubbed.

*Peduncle.* — Length — short. Aspect — smooth. Strength—stiff.

Bud opens well.

Bloom:

*Size.*—Large. Average size when fully expanded—5".

*Borne.*—In clustersand irregular.

*Stems.*—Long and normal.

*Form.*—When first open—flat. Permanence—retains its form to the end.

*Petalage.*—Very double with many petals and stamens hidden. Number of petals under normal conditions—too numerous to count.

*Color.*—Center of flower—10YR 8/10. Outer petals—7.5YR 8/8. Base of petals—2.5YR 6/12. Inside of petals—7.5YR 8/8. Reverse of petals—10YR 8/10. General tonality from a distance—5YR 6/11, shading into 7.5YR 8/8.

*Discoloration.*—General tonality at end of: First day—5YR 6/11 shading into 7.5YR 8/8. Second day—2.5Y 8/12 shading into 2.5Y 9/9. Third day—5Y 8/12 shading into 5Y 9/9.

Petals:

*Texture.*—Thick. Affected by wet weather with rotting tendency and burns in hot weather.

*Appearance.*—Inside—shiny. Outside—shiny.
*Form.*—Flat.
*Arrangement*—Imbricated.
*Petaloids in center.*—Many.
*Persistence.*—Hang on and dry.
*Lastingness.*—On the plant—very long. As cut flower—very long.

Genital organs:
*Stamens, anthers.*—Small, many. Arrangement—regular around styles.
*Stamens, filaments.*—Short.
*Styles.*—Columnar and short.
*Ovaries.*—Protruding from calyx.

Fruit: Variety is fertile with its own pollen.
*Form.*—Seeds protruding.
*Aspect.*—Rough and hairy.
*Sepals.*—Recurved.

Plant:
*Form.*—Bush.
*Growth*—medium and branching.
*Height.*—Approximate measurements of average plant 24 inches with 30 inch spread.

Foliage:
*Leaflets.*—Single leaves.
*Size.*—Large.
*Quantity.*—Normal.
*Color.*—Upper side—10GY 4/5. Under side—7.5GY 5/7.
*Shape.*—Lobed.
*Texture.*—Upper side—glossy.
*Ribs and veins.*—Ordinary.
*Edge.*—Undulated.
*Leaf stem.*—Under side—smooth.
*Stipules.*—Short and smooth.

I claim:

A new and distinct variety of chrysanthemum plant substantially as herein disclosed, characterized as to novelty by its more tightly incurving blooms, the strong orange shading into moderate orange yellow color of the blooms, its upright compact growth, its bushy plant habit and early profuse and continuous blooming habit.

No references cited.